(12) United States Patent
Saarenmaa et al.

(10) Patent No.: US 9,207,228 B2
(45) Date of Patent: Dec. 8, 2015

(54) MEASUREMENT OF AMOUNT OF SOLID IN SUSPENSION

(75) Inventors: Sami Saarenmaa, Pirkkala (FI); Marko Heikkinen, Muhos (FI); Matti-Paavo Saren, Kajaani (FI); Arvo Rahikkala, Kajaani (FI)

(73) Assignee: VALMET AUTOMATION OY, Espoo (FI)

( * ) Notice: Subject to any disclaimer, the term of this patent is extended or adjusted under 35 U.S.C. 154(b) by 8 days.

(21) Appl. No.: 13/988,627

(22) PCT Filed: Nov. 29, 2011

(86) PCT No.: PCT/FI2011/051057
§ 371 (c)(1),
(2), (4) Date: May 21, 2013

(87) PCT Pub. No.: WO2012/072880
PCT Pub. Date: Jun. 7, 2012

(65) Prior Publication Data
US 2013/0249569 A1    Sep. 26, 2013

(30) Foreign Application Priority Data
Nov. 30, 2010    (FI) .................................. 20106260

(51) Int. Cl.
*G01R 27/28* (2006.01)
*G01N 33/34* (2006.01)
*G01N 15/06* (2006.01)
*G01N 27/04* (2006.01)

(52) U.S. Cl.
CPC ............ *G01N 33/34* (2013.01); *G01N 15/0656* (2013.01); *G01N 27/041* (2013.01); *G01N 33/343* (2013.01)

(58) Field of Classification Search
CPC .. G01N 15/0656; G01N 33/343; G01N 33/34
USPC ................................. 324/600, 629–647, 71.4
See application file for complete search history.

(56) References Cited

U.S. PATENT DOCUMENTS 4,483,199 A  *  11/1984  Beiermann et al. ........ 73/861.04
4,770,232 A  *   9/1988  Chubb ............................ 165/41
(Continued)

FOREIGN PATENT DOCUMENTS

| CN | 101374592 A | 2/2009 |
|---|---|---|
| JP | H06-114062 A | 4/1994 |
| JP | A-7-190928 | 7/1995 |

(Continued)

OTHER PUBLICATIONS

Jul. 7, 2014 English language version of Office Action issued in Chinese Application No. 201180057589.3.

(Continued)

*Primary Examiner* — Melissa Koval
*Assistant Examiner* — Trung Nguyen
(74) *Attorney, Agent, or Firm* — Oliff PLC (57) ABSTRACT

A measuring part measures the amount of matter dispersed in a suspension on the basis of a measurement, in which electromagnetic radiation interacts with the suspension, and the proportional volume of a free gas contained in the suspension on the basis of a measurement of electrical conductivity and/or impedance distribution for determining the amount of dispersed solid matter in the suspension.

10 Claims, 6 Drawing Sheets

(56) References Cited

U.S. PATENT DOCUMENTS

2002/0066304 A1    6/2002   Jakkula et al.
2006/0228590 A1* 10/2006  Hashimoto et al. ........ 428/840.5

FOREIGN PATENT DOCUMENTS

| JP | 2010-107487 A | 5/2010 |
|---|---|---|
| WO | WO 02/053029 A1 | 7/2002 |
| WO | WO 2004/077036 A1 | 9/2004 |

OTHER PUBLICATIONS

Zhou et al., "Impedance Tomography," *Multiphase flows in process industry*, 2005, pp. 80-96, Espoo.

Seleghim Jr. et al., "Direct imaging of two-phase flows by electrical impedance measurements," *Meas. Sci. Technol.*, 1998, pp. 1492-1500, vol. 9, IOP Publishing Ltd., United Kingdom.

International Search Report issued in International Patent Application No. PCT/FI2011/051057 dated Mar. 12, 2012.

Finnish Search Report issued in Finnish Patent Application No. 20106260 dated Jun. 23, 2011 (w/translation).

International Preliminary Report on Patentability issued in International Patent Application No. PCT/FI2011/051057 dated Apr. 16, 2013.

May 20, 2015 Search Report issued in European Application No. 11845071.7.

Liter et al., "Sand Report Electrical-Impedance Tomography for Opaque Multiphase Flows in Metallic (Electrically Conducting) Vessels", Nov. 1, 2002, pp. 1-84, http://www.fischer-tropsch.org/DOE/DOE_reports/sandia_bubble_col/2002-3834/litersand2002-3834.pdf.

Kataja, "Multiphase Flows in Process Industry: ProMoni", vol. 2286, Jan. 1, 2009, pp. 1-185, http://www.vtt.fi/inf/pdf/tiedotteet/2005/T2286.pdf.

Heikkinen et al., "Utilizing Prior Information in the Estimation of Volume Fraction Distribution", International Journal for Numerical Methods in Engineering, vol. 63, No. 12, Apr. 18, 2005, pp. 1719-1740.

Aug. 11, 2015 Office Action issued in Japanese Application No. 2013-541395.

* cited by examiner

MEASUREMENT OF AMOUNT OF SOLID IN SUSPENSION

FIELD

The invention relates to measurement of the amount of solid matter dispersed in a suspension.

BACKGROUND

In particular, in paper and pulp industry it is important to be able to measure slush consistency, because the consistency indicates the proportion of a solid in the slush. The amount and quality of the solid matter, in turn, have a crucial effect on the properties and quality of paper or board obtained as a final product.

The slush is a suspension the consistency of which may be measured by means of electromagnetic radiation, for instance. The consistency may be determined by means of the attenuation of the electromagnetic radiation, the radiation being in interaction with the suspension. The electromagnetic radiation may in that case be radio-frequency or optical radiation. The consistency may also be measured, for instance, by means of the propagation time of radio-frequency radiation. In both measurements the radio-frequency radiation or the optical radiation either goes through the suspension or reflects therefrom. Corresponding suspension measurements may also be carried out in other fields of industry.

The measurement of the amount of solid in the suspension is disturbed, however, by air or another gas present in the suspension, which gets into, or possibly, is intentionally added to the suspension in industrial processes. Hence, the measurement of the amount of solid in the suspension becomes inaccurate.

BRIEF DESCRIPTION

It is the object of the invention to provide an improved solution for measuring the amount of solid in a suspension.

This is achieved by a device for measuring the amount of solid in the suspension. The device comprises a measuring part, which is arranged to determine the amount of matter dispersed in the suspension on the basis of a measurement, in which electromagnetic radiation is arranged to interact with the suspension, and the proportional volume of a free gas contained in the suspension on the basis of a measurement of electrical conductivity and/or impedance distribution for determining the amount of dispersed solid matter in the suspension.

The invention also relates to a method for measuring the amount of solid in a suspension, characterized by measuring the amount of solid in the suspension through a measurement in which electromagnetic radiation interacts with the suspension; measuring a proportional volume of a free gas contained in the suspension on the basis of the measurement of electrical conductivity and/or impedance distribution in the suspension; and providing the amount of the solid dispersed in the suspension on the basis of the amount of the dispersed solid and the proportional volume of the free gas.

Preferred embodiments of the invention are disclosed in the dependent claims.

Several advantages are achieved by each solution of the invention. The amount of solid in the suspension may be measured accurately, which enables improved quality in a final product.

LIST OF FIGURES

The invention will now be described in greater detail in connection with preferred embodiments, with reference to the accompanying drawings, in which.

DESCRIPTION OF EMBODIMENTS

The presented solution may be applied, for instance, to pulp processing, paper or board making, processes relating to recycled fibre pulps, fields of industry associated with environmental management, such as purification of waste water and/or the like, without restricting to said examples, however.

A suspension comprises a liquid medium with solid particles dispersed therein. In addition, the suspension in the embodiments of this application may also contain dispersed gas, such as air. The medium is usually water, but in a general case the medium may also consist of some other liquid. Consistency of the suspension may vary from zero to tens of percent. In paper industry, the consistency is often 0.1% to 20%. The amount of dispersed substance in a suspension may be measured in volumetric percent or mass percent. When expressed in volumetric percent, the volume of the dispersed matter is divided by the total volume of the suspension and multiplied by 100%. When expressed in mass percent, the mass of the dispersed matter is divided by the total mass of the suspension and multiplied by 100%.

Especially in applications of paper and pulp industry the solid in the suspension may consist of fibres, for instance. In paper and board industry, the fibre is often wood fibre. However, the fibre may be any fibre, such as animal fibre, plant fibre, cellulose-based fibre or artificial fibre. The slush used in paper and board making is a suspension the medium of which is water and the solid particles may be fibres, fines, fillers, retention agent, coating agent, ink, etc.

Solid matter in waste water to be purified may be, for instance, sand, paper, nutrients and various precipitates or sludge.

The measurement of the amount of solid is based on the fact that the measurement of electromagnetic radiation is affected by different proportional dielectric constants of the solid particles and the medium. The more solids in the suspension, the more the measurement result differs from the measurement result of the medium alone. The measurement of the amount of solid is disturbed by the fact that the medium and a gas may have mutually different proportional dielectric constants. Thus, both the medium and the gas have a concurrent effect on the measurement result, and no accurate data on the amount of solid will be obtained.

FIGS. 1A to 4B show a solution, which is based on the fact that a measuring part 150, 152, 250, 252, 350 determines the amount of dispersed matter in a suspension 106 on the basis of the measurement where electromagnetic radiation interacts with the suspension 106. In addition, the measuring part 150, 152, 250, 252 determines a proportional volume of a free gas 318 contained in the suspension on the basis of electrical conductivity and/or impedance distribution in the suspension 106.

Figure 1A:
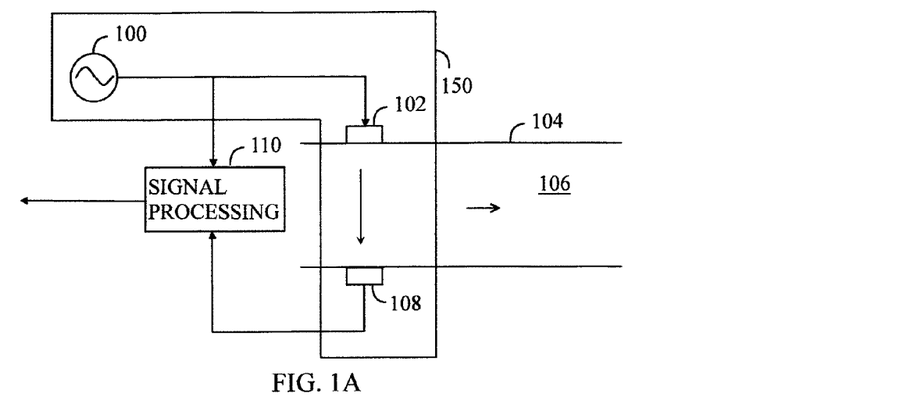
FIG. 1A shows measurement performed by radio-frequency electromagnetic radiation through a suspension.

FIG. 1A shows a measurement of the amount of solid, such as consistency, by using radio-frequency electromagnetic radiation. Generally, the measurement of the amount of solid may refer to volumetric proportion or weight proportion of the solid in a given volume. In a measuring arrangement, a radio-frequency source 100, such as a radio-frequency oscillator, may scan the frequency of a transmitting radio-frequency electromagnetic signal over a desired frequency band.

In the solution it is possible to use the FMCW (Frequency Modulation Continuous Wave) method. The frequency of the electromagnetic radiation generated by the radio-frequency source 100 may be 100 MHz to 100 GHz, for instance. The frequency band used in measuring may be a few hundred megahertzes, for instance. Scanning may be performed, for instance, such that the frequency of a transmitted radio-frequency signal increases from initial frequency $f_0$ to highest frequency $f_{max}$ and thereafter the frequency decreases from the highest frequency $f_{max}$ back to the initial frequency $f_0$. Frequency scanning of this kind may be repeated throughout the measurement. The frequency may increase or decrease continuously or discretely. The scan length is not critical to the invention, but, in practice, the duration of a frequency scan may be 1 ms to 100 ms, for instance.

A signal from the radio-frequency source 100 propagates to a feed element 102, which may be attached to a pipe 104 or which may be, for instance, an antenna, such as a slot antenna, a flat panel antenna or a patch antenna. A feeding contact element 102 applies a signal through a suspension 106 flowing in the pipe 104 to a receiving contact element 108, whereby electromagnetic radiation interacts with the suspension 106. The signal that traversed the suspension 106 propagates through a detecting contact element 108 to a signal processing unit 110, which compares the electromagnetic signal directed to the suspension 106 with the signal that has interacted with the suspension 106. A measurement parameter may be a signal transit time, frequency or phase. The contact elements 102, 108 may be attached to the pipe 104.

The signal processing unit 110 may, for instance, determine the transit time of the signal traversed through the suspension 106 and/or the attenuation thereof in relation to the signal coming directly from the source 100. Blocks 100, 102 and 108 thus constitute the measuring part 150 for measuring solid matter in the suspension 106.

The measurement may be performed as a direct transit time measurement by means of a signal pulse by measuring the time between the transmission and reception of a pulse. This is a commonly used measuring technique, for instance, in level measurings, in which the distance of a reflective surface from a transceiver antenna is computed on the basis of a measured transit time.

The signal transit time through the suspension 106 may also be determined by means of the phase difference between the signal applied to the suspension 106 and the signal traversed through the suspension.

The difference in delay $\Delta t$ between the signal traversed through the suspension and the signal applied to the suspension is expressed $$\Delta t = f * T/B,$$

where f is frequency of signal, B is band width of frequency scanning (Hz) and T is duration (s) of frequency scanning.

The phase difference may also be determined by measuring the phase of one or more dot frequencies passed through a measurement path, when frequency scanning is not used. This may be implemented, for instance, by a so-called heterodyne technique, which produces a value based on the phase difference between a signal applied to the suspension and a radio-frequency signal traversed through the suspension. Because a generator 100 may output a constantly unchanged signal, phase changes in the signal traversed through the suspension 106 may be measured directly.

It is possible to determine the transit time also by a correlation technique. The correlation measurement attempts to find the highest possible correlation by shifting the signal applied to the suspension 106 and the signal traversed through the suspension in relation to one another. How much the signals are to be mutually shifted temporally in view of the measuring moment in order to provide the highest possible correlation, determines the difference in transit times between the signal applied to the suspension and the signal traversed through the suspension.

The signal processing unit or the signal processing part may provide the correlation $C(\tau)$ for instance as follows:

$$C(\tau) = \int x(t) \cdot y(t-\tau) dt$$

where x(t) is a first detected signal and y(t−τ) is a second detected signal that has been delayed for the amount of τ. The value of correlation is computed with a plurality of delay values such that $\tau \in [t_0, \ldots, t_n]$, where $t_0$ is the shortest possible delay and $t_0$ is the longest possible delay.

Because the transit time and the phase are directly proportional to one another, the amount of solid, such as consistency, may be computed on the basis of either one of them. The connection between the transit time $\Delta t$ and the phase $\phi$ may be expressed, for instance, by equation $$\Delta t = n * T_f + \phi / 2\pi * T_f,$$

where $T_f$=period length of the frequency used, n=the number of full period lengths on a measurement path, $\phi$=signal phase and $\pi \approx 3.14159265$.

Because the phase depends on the transit time, hereinafter only the transit time is referred to, even though the measurement could be made per se using a phase.

A measurement parameter may also be signal strength, and therefore, instead of or in addition to the transit time, the signal processing unit 110 may determine a change in the strength of radio-frequency electromagnetic radiation, i.e. attenuation, when the electromagnetic radiation is in interaction with the suspension 106. Solid particles and gas bubbles present in the suspension 106 attenuate the radio-frequency electromagnetic radiation in the suspension 106. The higher the amount of solid particles and/or gas bubbles the electromagnetic radiation collides with in the suspension, the lower its strength becomes. The strength of radiation may be measured, for instance, as intensity (P/A, where P is power e.g. in watts and A refers to a detecting surface area e.g. in square meters).

Figure 1B:
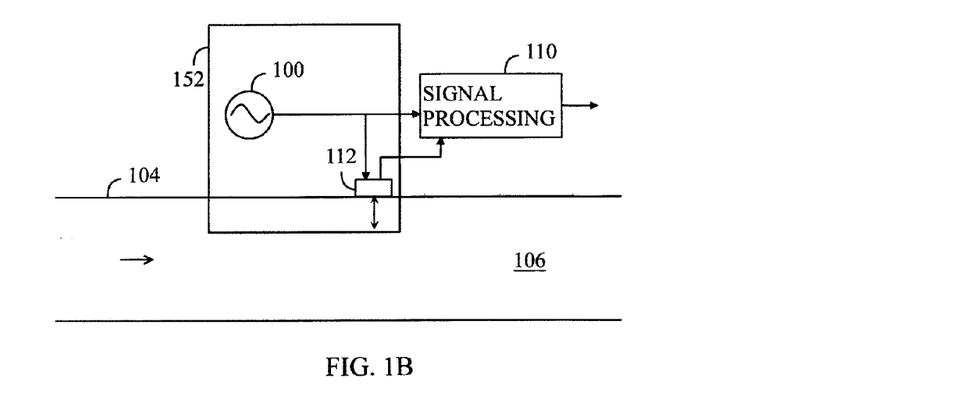
FIG. 1B shows reflection measurement in a suspension performed by radio-frequency electromagnetic radiation.

FIG. 1B shows an embodiment, in which the radio-frequency radiation generated by the source 100 is directed to the suspension 106 with a contact element 112, which also receives and detects the radiation reflected from the suspension 106. The contact element 112 may be a transceiver antenna. Otherwise the comparison between the radiation interacted with the suspension 106 and the radiation applied to the suspension may be performed in the signal processing unit 110 like in the case of FIG. 1A. Blocks 100 and 112 thus constitute the measuring part 152 for measuring solid matter in the suspension 106.

In addition to or instead of radio-frequency measurement it is possible to use optical electromagnetic radiation for measuring the amount of solid in a suspension. Solid particles and gas bubbles present in the suspension 106 attenuate the optical radiation in the suspension 106. The higher the amount of solid particles and/or gas bubbles the optical radiation collides with in the suspension, the lower its strength becomes. In the same way as the strength of radio-frequency radiation also the strength of optical radiation may be measured, for instance, as intensity I (I=P/A, where P is power e.g. in watts and A refers to a detecting surface area e.g. in square meters).

Figure 2A:
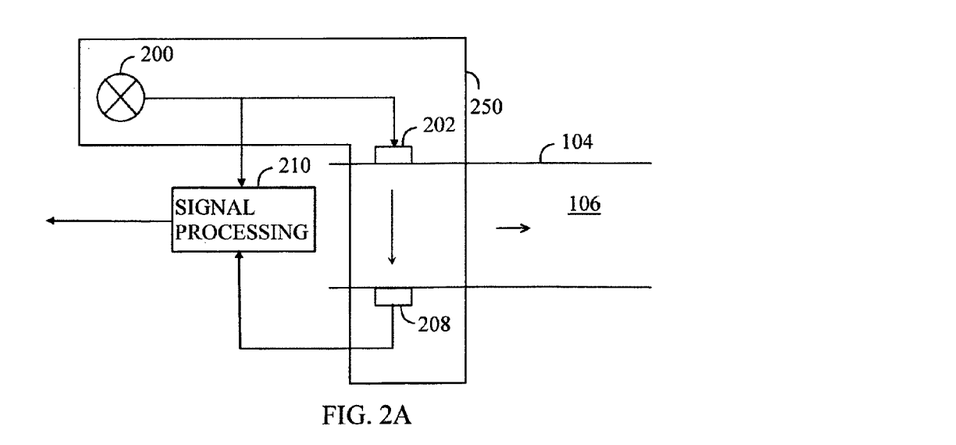
FIG. 2A shows optical measurement through a suspension.

FIG. 2A shows an embodiment, in which a source of optical radiation 200 applies optical radiation towards a feeding contact element 202, which is attached to a pipe 104, for instance. The contact element 202 directs the optical radiation to the suspension 106. Upon interacting with the suspension 106 on its way through the suspension 106 an input contact element 208 receives the optical radiation and conveys it to a signal processing part 210 to which it is also possible to apply a predetermined part of the optical radiation of the optical radiation source 200. The signal processing unit 210 may thus determine the attenuation of the optical radiation in the suspension 106. The optical radiation source 200 may apply optical radiation to the contact element 202 through an optical fibre. It is also possible that the optical radiation source 200 is located in the contact element 202, and consequently the optical radiation source 200 directs optical radiation directly to the suspension 106. A detecting contact element 208 may be an end of the optical fibre, at which there may be at least one optical component, such as a lens. The optical fibre may transfer the received optical radiation to the signal processing unit 210. The input contact element 208 may also be a detector of optical radiation which converts the optical radiation to an electric signal. The signal processing unit 210 may thus receive the electric signal provided by the detector, which conveys information on the strength of the optical signal. Blocks 200, 202 and 208 thus constitute the measuring part 250 for measuring solid matter in the suspension 106.

Figure 2B:
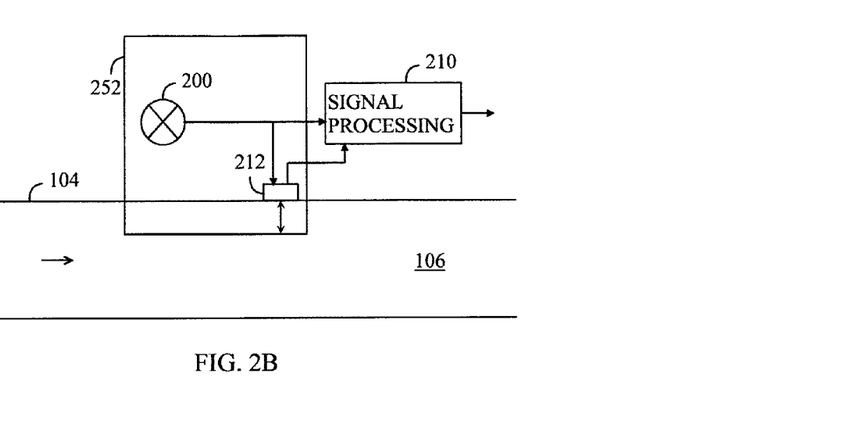
FIG. 2B shows optical reflection measurement on a suspension.

FIG. 2B shows the solution of FIG. 1B implemented in an optical manner. The optical radiation generated by the optical radiation source 200 is directed to the suspension 106 with a contact element 212, which also receives and detects the radiation reflected from the suspension 106. Otherwise the comparison between the radiation interacted with the suspension 106 and the radiation applied to the suspension may be performed in the signal processing unit 110 like in the case of FIG. 2A. Blocks 200 and 212 thus constitute the measuring part 252 for measuring solid matter in the suspension 106.

Even though in FIGS. 1A to 2B the radiation is indicated to travel transversely to the flow direction/pipe 104, the measurement of the amount of solid may also be carried out in longitudinally to the flow direction/pipe 104 directly or obliquely.

Figure 3A:
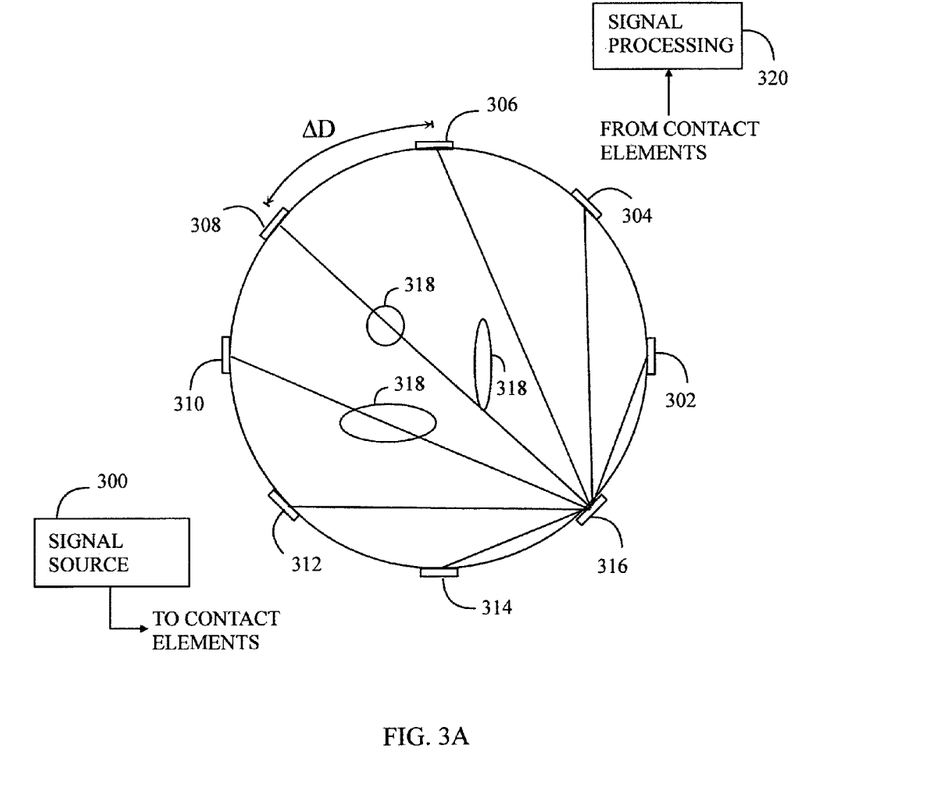
FIG. 3A shows impedance tomographic measurement on a suspension, one feeding contact element being active.

By means of FIG. 3A it is now examined measurement of proportional volume of free gas in connection or integrated with the measurement of the solid, which measurement measures distribution of impedance and/or electrical conductivity. The measurement may be based on impedance tomography, for instance. A signal source 300 may apply an electric signal to each contact element 302 to 316 separately at a specific time instant. Each two successive contact elements 302 to 316 may be at the same, or different, distance AD from one another as the other successive contact elements. The electric signal may be and an AC signal whose frequency may be lower than that of the radio-frequency signal. In FIG. 3A, the contact element 316 applies an electric signal to the suspension 106, and with other contact elements 302 to 314 the electric signal is received, and the signal, or a measurement value measured on the signal, is transferred from the contact elements to the signal processing part 320. While passing through the suspension, the electric signal may come to interaction with one or more gas bubbles 318, each of which affects the electric signal. When receiving the electric signal, the contact elements 302 to 314 may receive an electric signal that the signal processing unit 320 may compare with the electric signal applied to the suspension 106 by the contact element 316 and thus provide conductivity and/or impedance of the suspension 106 between each contact element 302 to 314 and 316. Conductivity and impedance are interdependent variables. In the measurement there is often determined impedance, wherefrom conductivity will be obtained. Conductivity and impedance may be understood to be inverse values of one another, for instance.

The obtained conductivities and/or impedances represent the distribution of electrical conductivity and/or impedance through the suspension 106. In the conductivity and/or impedance, it is possible to take into account both a resistive component and a reactive component, either together or separately.

Figure 3B:
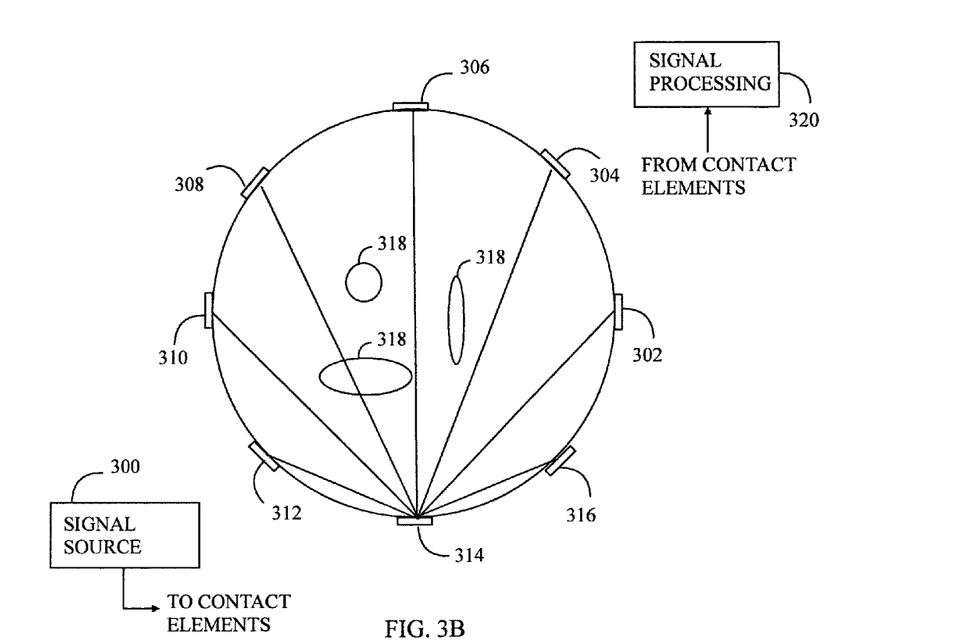
FIG. 3B shows impedance tomographic measurement on a suspension with a second contact element.

FIG. 3B also shows an impedance tomographic measurement. In this example the contact element 314 serves as an electric signal transmitter. When different contact elements are employed to apply the signal, the gas bubbles 318 present in the suspension appear in different gas bubble configurations in the measurement between the contact elements 302 to 316, which enables determination of bubble properties. The signal processing part 320 may detect a change in interaction, resulting from the location of the gas bubbles, in the impedance between the feeding contact element and each receiving contact element. All gas bubbles, and particularly their interfaces with the suspension, the size, such as diameter, cross-sectional area and/or volume, may change the impedance between the contact elements. After completing the impedance measurements between several or all contact elements 302 to 316, the shape, size and amount of gas bubbles 318 possibly present in the measuring area, and the amount of bubble interfaces, may be estimated. Estimation may be based, for instance, on a tomographic representation or the like on the suspension 106 and at least one gas bubble possibly present therein. Even without a tomographic representation the signal processing unit 320 may provide a total volume of possible one or more gas bubbles 318 in a measuring area which in the example of FIGS. 3A and 3B is the cross section of the pipe 104. Namely, the determination of the proportional volume of free gas contained in the suspension 106 may be based on the fact that the signal processing unit 320 may detect impedance tomographically the distribution of electrical conductivity and/or impedance in the suspension 106, which forms a kind of cross-sectional view of the measuring volume. The cross section may be a predetermined or desired surface, in the direction of which the measurements are performed in the suspension. The gas bubbles 318 represent free, insoluble gas in the suspension, and the solution of FIGS. 3A and 3B allows measurement of the volumetric distribution of the suspension relative to the behaviour of electricity in the suspension, the electricity being connected to the suspension through a galvanic coupling.

If the electric signals fed by each particular contact element 302 to 316 are modulated and/or encoded to be different, so that they can be separated from one another also in the reception and/or signal processing, the impedance measurements of several or all contact elements 302 to 316 may be carried out simultaneously.

The contact elements 302 to 316 may be combined or integrated to form one whole with the contact elements 102, 108, 202, 208, 212. Likewise, the signal processing unit 320 may be combined or integrated to form one whole with the signal processing unit 110, 210. Further, the source 300 may be combined or integrated to form one whole with the source 100, 200.

Figure 5:
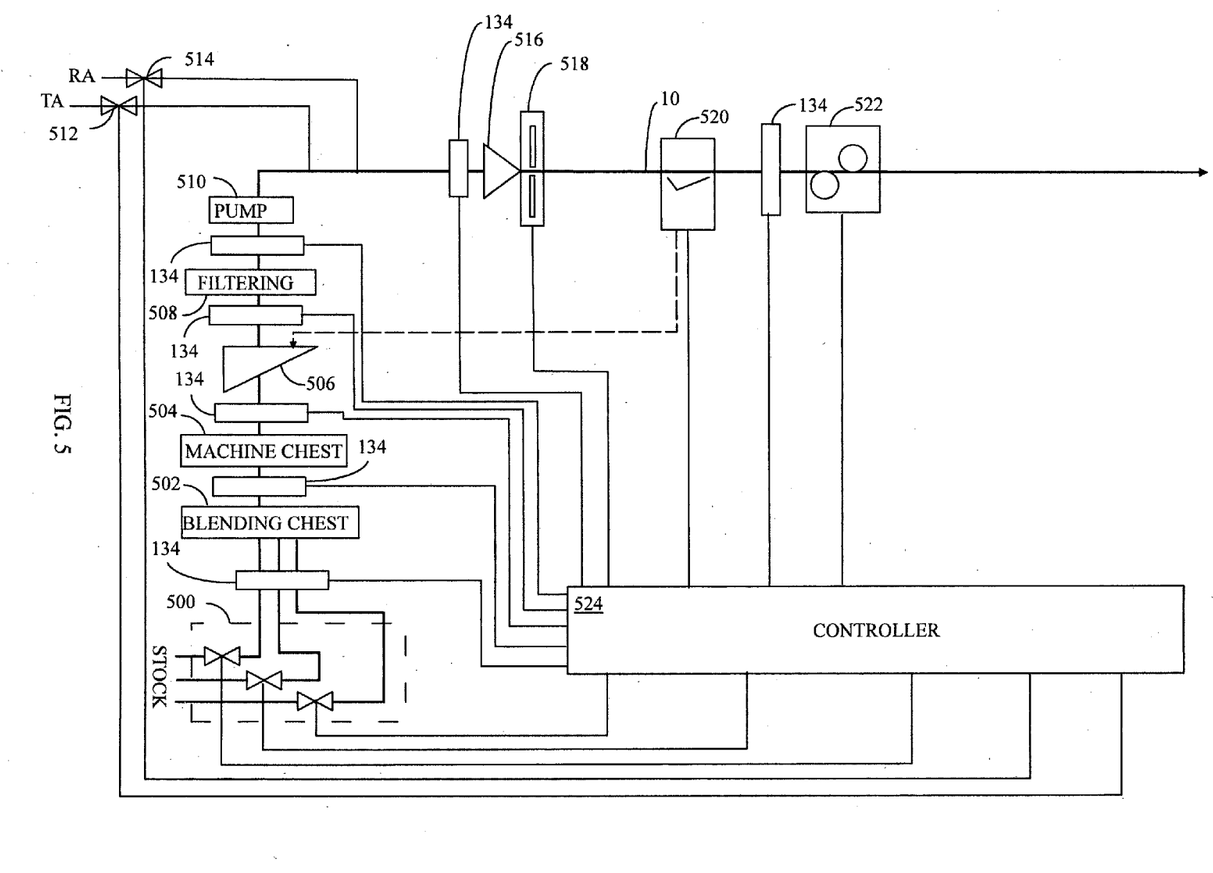
FIG. 5 shows a paper machine.
Figure 6:
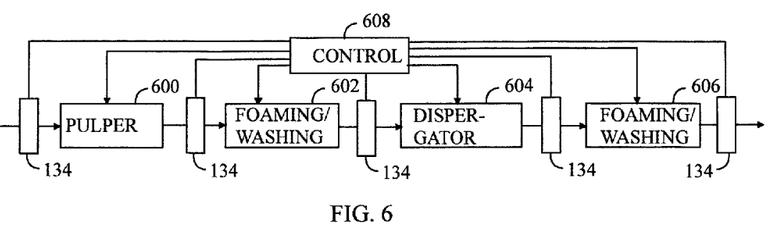
FIG. 6 shows a recycled fibre processing apparatus.
Figure 7:
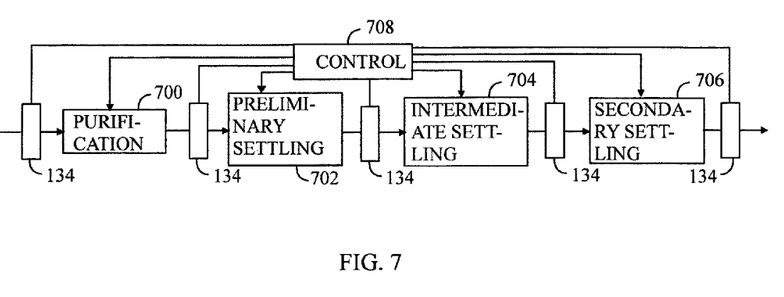
FIG. 7 shows a wastewater treatment plant.

The signal source 300, the contact elements 302 to 316 and the signal processing part 320 may constitute a second measuring part 350 measuring the proportional volume of gas, which second measuring part is not shown in the figures but which is referred to in the description of FIGS. 5, 6 and 7 and in the claims. In addition, the first measuring part and the second measuring part may be combined with one another and/or integrated to form one whole. Further, signal and/or data processing may be performed in separate signal processing parts or in a controller common to the whole process.

Figure 4A:
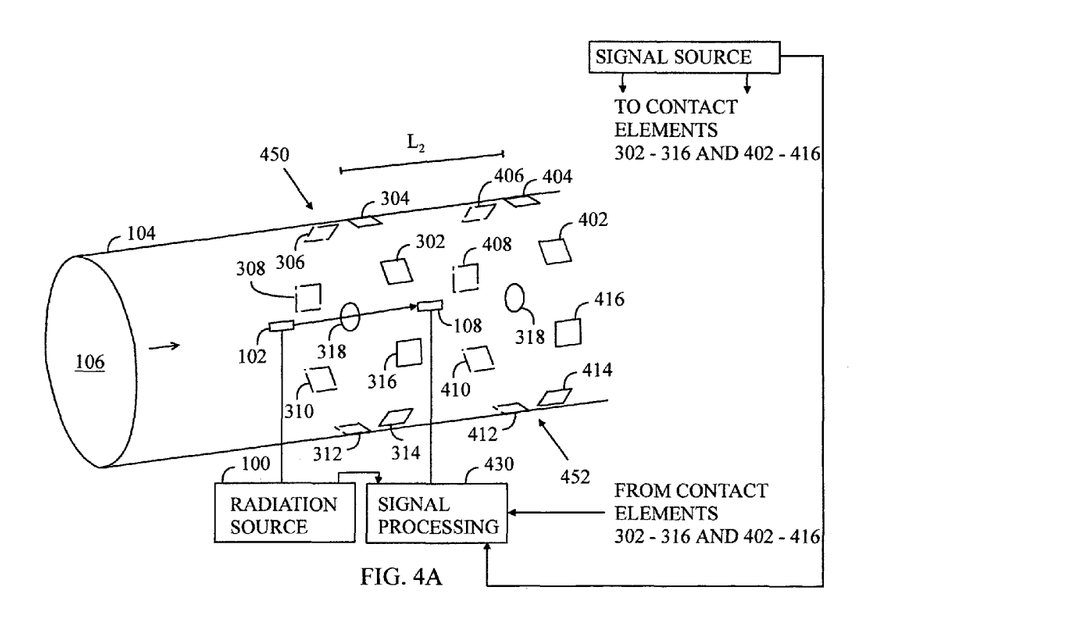
FIG. 4A shows a combination of the measurement of solid performed by electromagnetic radiation through the suspension and the impedance tomographic measurement of the amount of gas in the suspension.
Figure 4B:
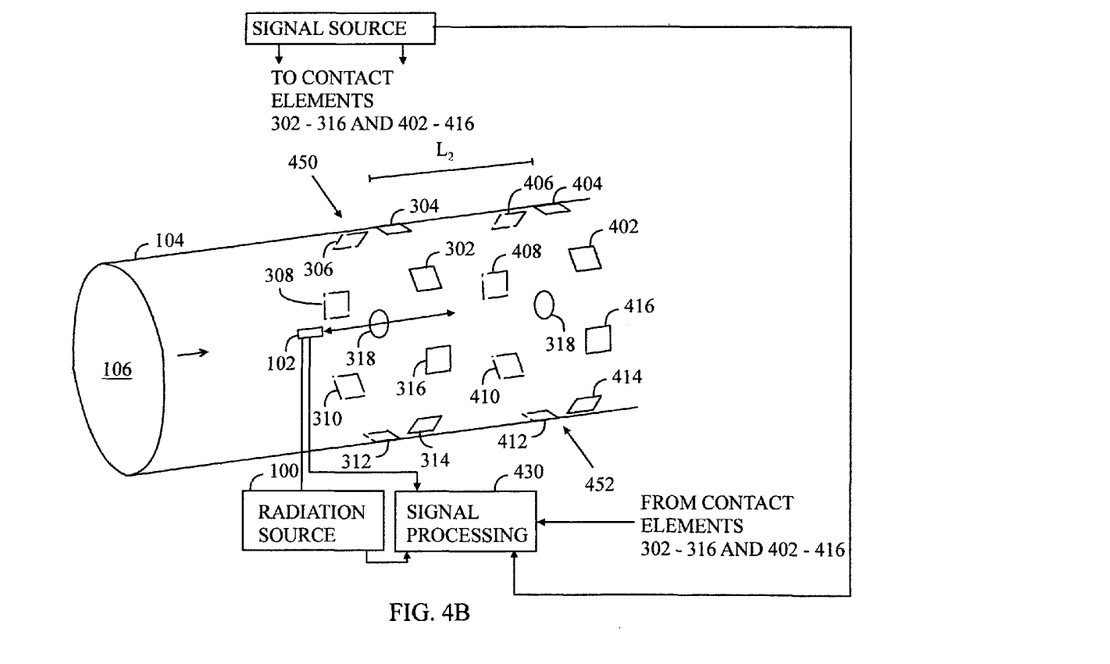
FIG. 4B shows a combination of the reflection measurement of the solid performed on the suspension by electromagnetic radiation and the impedance tomographic measurement of the amount of gas in the suspension.

The signal processing part, which is indicated in FIGS. 4A and 4B by reference numeral 430 and which is common to both the determination of the amount of solid and the determination of the proportional volume of free gas, may determine the amount of solid dispersed in the suspension 106 on the basis of the electromagnetic radiation measured by the first measuring part 150, 152, 250, 252 and the electrical conductivity and/or impedance distribution in the suspension 106 provided by the measurement with the second measuring part 350. The first and the second measuring parts constitute the pair of measuring parts 134, which appears in FIGS. 5, 6 and 7.

Figure 3C:
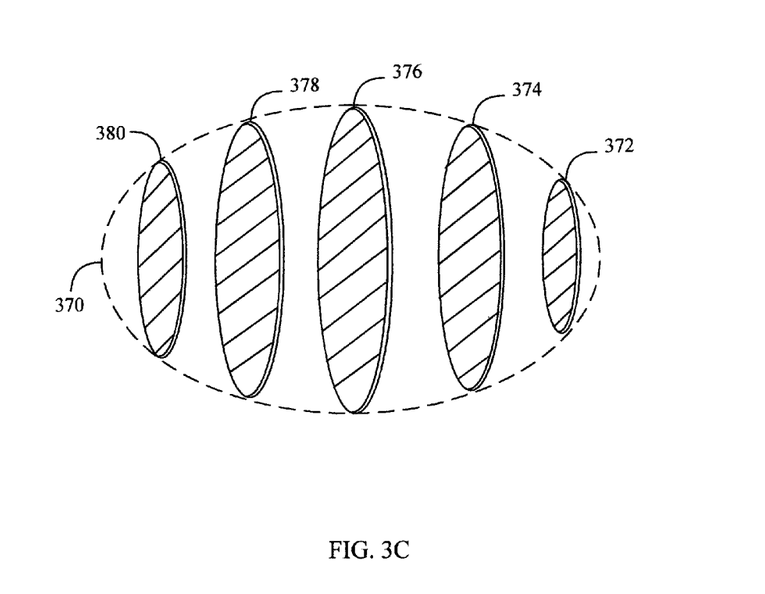
FIG. 3C shows a detected gas bubble.

FIG. 3C shows successive section views of a gas bubble which propagates along with the suspension flow past the measuring point. At a measuring time instant T1 the end of a bubble 370 hits the measuring point, when a first section view 372 is provided. The gas bubble 370 is indicated by a broken line. At a second measuring time instant T2 the gas bubble has propagated along with the flow, when a second section view 374 is provided. At a third measuring time instant T3 there is provided a third section view 376, which in this example coincides with the centre of the bubble 370. At a fourth measuring time instant T4 there is provided a section view 378 which resembles to a great extent to that of the measuring time instant T2. The last section view 380 of the bubble 370 is provided at a measuring time instant T5. By means of the section views 372 to 380 it is possible to provide a length estimate of the bubble 370 in the flow direction. Thickness estimates, in turn, may be provided directly from each section view 372 to 380. In this manner it is possible to determine, in a general case, the dimensions, shapes and amount of interfaces of the gas bubbles, in addition to the amount of the gas bubbles.

In addition to the proportional volume, the measuring part 350 may determine the free gas 318 for at least one of the following: the amount of bubbles, the amount of interfaces between the bubbles and the suspension. Because the transit time and attenuation of the electromagnetic radiation depend on the amount of gas bubbles in the suspension 106, the measurement result of the amount of solid may be modified also by means of the amount of gas bubbles, in addition to the volumetric measurement of the free gas. The amount of gas bubbles may indicate the proportional amount of gas bubbles in a measured volume. Because the amount of interfaces between the gas bubbles and the suspension affects the propagation of the electromagnetic radiation in the suspension, the measurement result of the amount of solid may be modified also on the basis of the amount of said interfaces, in addition to or instead of the amount of gas bubbles. As a rule, the more bubbles and/or interfaces, the more the measurement result needs to be modified. However, the size of gas bubbles also affects the propagation of electromagnetic radiation through the suspension. For instance scattering, which affects both the transit time and the attenuation of the electromagnetic radiation, is generally at its strongest when the diameter of the gas bubbles is in the order of the wave length used in measuring. In general, scattering is lower when the size of the gas bubbles is further from the magnitude of the wave length.

FIG. 4A shows a combined measurement of solid and gas in the suspension 106. A device measuring the amount of solid by electromagnetic radiation may comprise a source 100 of electromagnetic radiation and a signal processing part 430, which may physically locate in the same device box. The signal processing part 430 refers to, or a part of the signal processing part 430 may be, the signal processing unit 320 (FIGS. 3A, 3B) and/or at least one of the signal processing units 110 and 210 (FIGS. 1A to 2B). The electromagnetic radiation may be applied by a cable, for instance, from the radiation source 100 to the contact element 102 wherefrom the electromagnetic radiation may proceed into the suspension 106. In the example of FIG. 4A the electromagnetic radiation does not pass transversely against the flow of the suspension 106, but in parallel with the flow. After interaction with the suspension 106, the electromagnetic radiation is received with the contact element 108 and the electromagnetic radiation, or a measurement parameter value thereof, is transferred to the signal processing part 430 through a cable, for instance. Also a signal applied to the contact element 102, a known part thereof or information on the measurement parameter value of the signal, may be inputted as a reference into the signal processing part 430 in order to determine a change in the electromagnetic signal caused by the effect of the suspension 106. Alternatively, a measurement result obtained by the contact element 108 may be used as reference for determining changes in other measurement results.

In the interaction area of the electromagnetic radiation and the suspension 106 it is simultaneously possible to carry out also an impedance tomographic measurement of proportional volume of free gas. In practice, the interaction area covers a volume in the suspension 106, where both measurements are carried out. The pipe 104 may be encircled with more than one contact elements used for the measurement of the proportional volume of the gas such that at least two contact elements are side by side. FIG. 4B shows as an example two circles 450, 452 of contact elements 302 to 316 and 402 to 416. It is not necessary, however, to use actual, separate circles, but instead of the separate circles the contact elements may be placed spirally round the pipe 104. Thus is provided a structure of contact elements, in which there are contact elements both successively and adjacently. The use of a plurality of adjacent contact elements round the pipe 104 makes it possible that the signal processing part may form a kind of cross sectional view of the suspension 106 in a space between the adjacent contact elements 302 to 316 and 402 to 416. The mutual distance $L_2$ between the adjacent contact elements may be in the order of a distance $\Delta L$ between two immediately successive contact elements, the distance between every second successive contact element, or more. The mutual distance $L_2$ between the adjacent contact elements may also be shorter than the distance $\Delta L$ between two immediately successive contact elements.

The signal processing part 430 may provide the amount of solid dispersed in the suspension 106 accurately, for instance, such that when measuring the total amount of both free gas and solid matter in the suspension 106 by electromagnetic radiation, the resulting representative value, measured by means of electromagnetic radiation, is corrected by the proportional volume of free gas, which is obtained by the measurement of impedance tomographic electrical conductivity and/or impedance distribution. The correction may be made by modifying the calculation of the amount of solid adaptively in the signal processing part 430 such that the end result produces an amount of solid in the suspension 106, where the effect of free gas is reduced or removed. The correction may also be made such that the signal processing part 430 produces the total amount of solid matter and gas through measurement performed by electromagnetic radiation. Likewise, the signal processing part 430 produces the proportional volume of free gas through measurement of electrical conductivity and impedance distribution. Thereafter the signal processing part 430 may modify, if necessary, the data relating to the amount of solid matter and the volume of free gas to be relative or absolute values. The signal processing part 430 may subtract, from the produced total amount of solid and gas the produced amount of free gas, whereby there will remain the actual amount of solid matter in the suspension 106.

The signal source 300, the contact elements 302 to 316, 402 to 416 and the signal processing part 320 may constitute a measuring part 350 measuring the proportional volume of gas, which measuring part is referred to in the description of FIGS. 5, 6 and 7 and in the claims, but which is not shown in the figures.

FIG. 4B shows a pair of measuring parts which is otherwise similar to that of FIG. 4A, but in the example of FIG. 4B the measurement to be performed by electromagnetic radiation is carried out as reflection measurement, which is presented in greater detail in FIGS. 1B and 2B. In this example, the signal processing part 430 may comprise a signal processing unit 110 or 210, or corresponding functions.

Next will be examined application fields of the presented solution. FIG. 5 shows the structure of a paper machine in principle. One or more stocks are fed onto a paper machine through a wire pit silo 506, which is usually preceded by a blending chest 502 for partial stocks and a machine chest 504. The machine stock is dispensed for a short circulation, for instance, controlled by a basis weight control or a grade change program. The blending chest 502 and the machine chest 504 may also be replaced by a separate mixing reactor (not shown in FIG. 5), and the dispensing of the machine stock is controlled by feeding each partial stock separately by means of valves or another flow control means 500. In the wire pit silo 506, water is mixed into the machine stock to obtain a desired consistency for the short circulation (dashed line from a former 520 to the wire pit silo 506). From the obtained stock it is possible to remove sand (centrifugal cleaners), air (deculator) and other coarse material (pressure filter) using cleaning devices 508, and the stock is pumped with a pump 510 to a headbox 516. Prior to the headbox 516, for improving the quality of the end product, it is possible to add to the stock, through valves 512, 514, a filling agent TA and/or a retention agent RA, which are solids and affect the consistency.

From the headbox 516 the stock is fed via a slice opening 518 to a former 520. In the former 520, water drains out of the web 10 and additionally solids, such as ash, fines and fibres, are led to the short circulation. In the former 520, the stock is fed as a web 10 onto a wire, and the web 10 is preliminarily dried and pressed in a press 522.

Measurement of moisture content may be considered included in the measurement principle of the amount of solid. Namely, the amount of solid and the moisture content are directly interdependent variables. If the moisture content is 45%, the amount of solid is 100%−45%=65%.

In this application, the web 10 is considered a suspension until the water content in the web 10 has decreased excessively. Generally, the web 10 is not actually a suspension after the press 522, and consequently the measurement method presented in this application will no longer be applicable after the press 522.

The paper machine may comprise, before each partial process 500 to 522, in each partial process 500 to 520 or after each partial process 500 to 520, at least one pair of measuring parts 134 by which it is possible to determine the consistency by means of electromagnetic radiation and on the basis of the electrical conductivity distribution of the proportional gas volume, in the above-described manner. The pair of measuring parts 134 comprises both the measuring part 150, 152, 250, 252 measuring the amount of solid by electromagnetic radiation and the measuring part 350 measuring the distribution of electrical conductivity.

FIG. 5 also shows a control arrangement of a paper machine. Factors affecting the quality and grade change include, inter alia, the amount and mutual proportion of partial stocks, the amount of filler, the amount of retention agent, machine speed, the amount of white water and drying capacity. The controller 524, which may receive measurement data from the signal processing part 430 or the part of which the signal processing part 430 may be, may control the dispensing of partial stocks by means of valves 500, the dispensing of each filler TA by means of the valve 512, the dispensing of the retention agent RA by means of the valve 514, adjust the size of the slice opening 518, control the machine speed, control the amount of white water and the drying process. The controller 524 may utilize one or more measuring part pairs 134 directly or through the signal processing part 430 so as to measure the stock and/or the web 10. The controller 524 may receive data on the stock and/or the web also from elsewhere (e.g. from the same points were controls are performed).

In addition to this, it is clear that the operation of a paper machine is known per se to a person skilled in the art, and therefore, it need not be presented in greater detail in this context.

Next will be examined a recycled fibre process, in general, by means of FIG. 6. At first, waste paper raw material, such as newspapers, advertising leaflets or periodicals, may be fed into a partial process of pulping 600, in a pulper of which the raw material is mixed with water such that the consistency of recycled fibre pulp will be e.g. 5 to 18%, depending on the pulping method used. The purpose of the partial process of pulping is to disintegrate the solid raw material into separate particles in a suspension. The pulper 600 may be, for instance, a rotating pulper that disintegrates pulp mechanically. Various chemicals may also be introduced into the partial process of pulping to detach particles from one another. Largest impurities and non-degradable objects, such as staples, pieces of plastic etc., may be filtered out and shifted onto a waste conveyor.

Next, the recycled fibre pulp may be washed in a partial process of washing 602. At this stage the consistency of the recycled fibre pulp is usually lowered to a level of about 1%, for instance. In washing it is possible to use foaming which removes small, free particles from the recycled fibre pulp.

Washing removes particles of all sizes, yet the most solid particles removed are in a size category of about 10 μm to 100 μm.

The task of a partial process of dispersing 604 is to further detach ink particles, still adhering to the fibres of the recycled fibre pulp, chemically and mechanically. For a mechanical treatment a dispersion machine in the partial process of dispersing includes a stator and a rotating rotor, the blades of which work the pulp. While passing through the blades the speed of the pulp changes fast, whereby the fibres are subjected to mechanical stress which detaches ink from the fibres. At the same time also smudges are to be removed and the particle size of ink particles is to be reduced.

Finally, the recycled fibre pulp may be washed once more in a second partial process of washing 606. Also in this washing it is possible to use foaming which removes small, free particles from the recycled fibre pulp.

Before each process, in each process and after each process there may be a pair of measuring parts 134, which comprises both a measuring part 150, 152, 250, 252 for measuring the amount of solid by electromagnetic radiation and a measuring part 350 measuring the amount of proportional gas volume. Each different partial process 600 to 606 of the recycled fibre process may be controlled by a controller 608, to which it is possible to input measurement results from different points of the recycled fibre process. The controller 608 may receive measurement data from each pair of measuring parts 134. It is also possible that the signal processing part 430, which is usually located in the pairs of measuring parts 134, is a part of the controller 608. The controller 608 may utilize one or more measuring part pairs 134 directly or through the signal processing part 430 placed in the controller 608 so as to measure the stock in different processes and/or therebetween. The controller 608 may utilize the measurement data on the partial processes when optimizing the operation of each partial process separately or when optimizing the cooperation of various partial processes in order to obtain a good end product.

FIG. 7 shows a wastewater treatment plant. A wastewater suspension may be fed along a pipe or the like to a mechanical purification process 700, in which easily separable solids, such as sand and large solid pieces, may be separated from the wastewater. The mechanical purification process 700 may comprise screening and possibly pre-aeration, for instance. Next the mechanically purified wastewater suspension may be transferred to a preliminary settling process 702, in which a sludge is allowed to deposit on the bottom of a settling pool used in the preliminary settling process 702. The deposited sludge may be dried or composted, for instance. The wastewater suspension may be transferred from the preliminary settling process 702 to an intermediate settling process 704, in which the wastewater suspension may be aerated, for instance, to reduce nitrogen in the wastewater. The aerated wastewater suspension may be further transferred to a secondary settling process 706, whereto it is possible to feed a precipitant such as ferrous sulphate. From the bottom of the pool included in the secondary settling process 706 the precipitated sludge may be recycled back to the preliminary settling process 702, for instance. The purified wastewater suspension, which now contains only little solid matter, may be conveyed to sea or further processing, for instance.

With the pair of measuring parts 134 the wastewater suspension may be measured, for instance, before the mechanical purification process 700, between every process 700 to 706, after the secondary settling process 706 and/or in each process 700 to 706. The pair of measuring parts 134 comprises both the measuring part 150, 152, 250, 252 measuring the amount of solid by electromagnetic radiation and the measuring part 350 measuring the proportional volume of gas.

Each different partial process 700 to 706 of the wastewater purification plant may be controlled by a controller 708, to which it is possible to input measurement results from various points of the wastewater treatment. The controller 708 may receive measurement data from each pair of measuring parts 134. It is also possible that the signal processing part 430, which is usually located in the pairs of measuring parts 134, is a part of the controller 708. The controller 708 may utilize one or more measuring part pairs 134 directly or through the signal processing part 430 placed in the controller 708 so as to measure the stock in different processes and/or therebetween. The controller 708 may utilize the measurement data on the partial processes when optimizing the operation of each partial process separately or when optimizing the cooperation of various partial processes in order to obtain as good an end product as possible.

It is described in the above that the suspension is transferred in the pipe 104. Instead of the pipe 104, it is also possible, however, to use another suspension transfer means. The transfer means may be, for instance, a channel having V- or U-shaped profile. In addition, the suspension 106 need not necessarily be transferred anywhere, but instead of the pipe 104, there may be a tank, in which the suspension is stored. In that case, in addition to the measurement of the amount of solid and the proportional volume of gas, it is possible to measure the suspension for convection currents or currents caused by blending.

The signal processing units 110, 210 and 320 and the signal processing part 430 as well as the controllers 524, 608 and 708 may comprise a processor, memory and an appropriate computer program for implementing the operations described to be carried out by these components.

Figure 8:
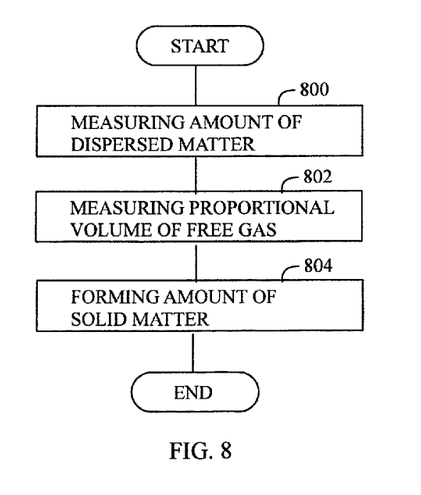
FIG. 8 is a flow chart of the method.

FIG. 8 is a flow chart of the method. In method step 800, the amount of the matter dispersed in the suspension 106 is determined on the basis of the measurement of the suspension 106, in which electromagnetic radiation interacts with the suspension 106. In step 802, a proportional volume of a free gas 318 contained in the suspension 106 is determined on the basis of measurement of electrical conductivity and/or impedance distribution in the suspension 106. In step 804, the amount of solid matter dispersed in the suspension 106 is provided on the basis of the amount of the dispersed matter and the proportional volume of the free gas 318.

The method shown in FIG. 8 may be implemented as a logic circuit solution or computer program. The computer program may be placed on a computer program distribution means for the distribution thereof. The computer program distribution means is readable by a data processing device, and it encodes the computer program commands, carries out the measurements and optionally controls the processes on the basis of the measurements.

The distribution medium, in turn, may be a medium readable by a data processing device, a program storage medium, a memory readable by a data processing device, a software distribution package readable by a data processing device, a signal readable by a data processing device, a telecommunications signal readable by a data processing device, or a compressed software package readable by a data processing device.

Even though the invention is described above with reference to the examples of the attached drawings, it is clear that the invention is not restricted thereto, but it may be modified in a variety of ways within the scope of the accompanying claims.

The invention claimed is:

1. A device for measuring the amount of solid in a suspension, the device comprising:
a first measuring part configured to direct electromagnetic radiation to the suspension and to measure the electromagnetic radiation interacted with the suspension in order to measure the amount of the dispersed matter in the suspension, the suspension including a liquid medium and solid particles and gas dispersed therein;
a second measuring part configured to measure at least one electrical conductivity and impedance distribution in the suspension impedance tomographically in order to determine a proportional volume of a free gas contained in the suspension; and
a signal processing part configured to form one or more cross-sectional views from the suspension and provide the amount of solid matter dispersed in the suspension on the basis of the amount of the dispersed matter and the proportional volume of the free gas in the one or more cross-sectional views formed from the suspension.

2. The device of claim 1, wherein, in addition to the proportional volume, the second measuring part is configured to determine on the free gas at least one of the amount of bubbles and the amount of interfaces between the bubbles and the suspension.

3. The device of claim 1, wherein the signal processing part is configured to determine the proportional total amount of the solid matter and the gas on the basis of electromagnetic radiation measurement,
the signal processing part is configured to determine the proportional volume of free gas in the suspension based on at least one of the electrical conductivity and the impedance distribution, and
the signal processing part is configured to subtract the determined proportional volume of free gas from the determined proportional total amount of the solid matter and the gas.

4. The device of claim 1, wherein the first measuring part is configured to measure the transit time of radio-frequency electromagnetic radiation.

5. The device of claim 1, wherein the first measuring part is configured to measure attenuation of optical electromagnetic radiation.

6. A method for measuring the amount of solid in a suspension, the method comprising:
measuring the amount of solid dispersed in the suspension in a measurement, in which electromagnetic radiation interacts with the suspension, the suspension including a liquid medium and solid particles and gas dispersed therein;
measuring a proportional volume of a free gas contained in the suspension on the basis of impedance tomographical measurement of at least one of electrical conductivity and impedance distribution in the suspension; and
forming one or more cross-sectional views from the suspension and providing the amount of solid matter dispersed in the suspension on the basis of the amount of the dispersed matter and the proportional volume of the free gas in the one or more cross-sectional views formed from the suspension.

7. The method of claim 6, the method further comprising:
measuring the electromagnetic radiation that has interacted with the suspension and determining the proportional total amount of the solid matter and the gas on the basis of said electromagnetic radiation measurement;
determining the proportional volume of free gas in the suspension based on at least one of the electrical conductivity and the impedance distribution; and
subtracting the determined proportional volume of free gas from the determined proportional total amount of the solid matter and the gas.

8. The method of claim 6, the method further comprising measuring the transit time of the radio-frequency electromagnetic radiation in order to determine the amount of the dispersed matter in the suspension.

9. The method of claim 6, the method further comprising measuring the attenuation of the optical electromagnetic radiation in order to determine the amount of the dispersed matter in the suspension.

10. The method of claim 6, the method further comprising measuring a flow of the suspension by comparing measurements performed at least at two different time instants with one another.

* * * * *